Figure 1A:
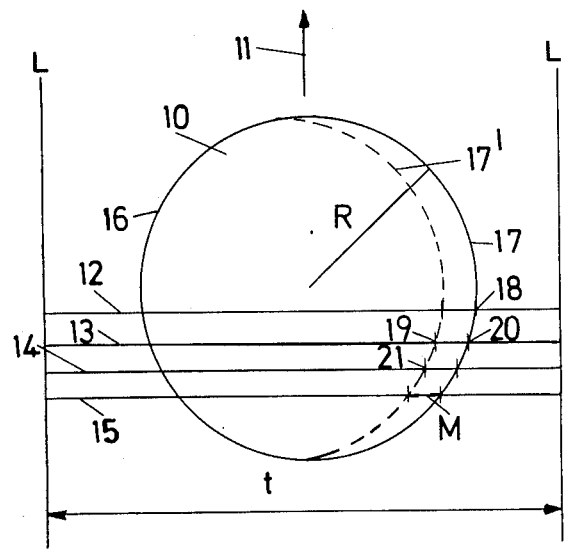

United States Patent [19]

Clarke

[11] 4,014,615
[45] Mar. 29, 1977

[54] DETECTION OF FAULTS IN A PREDETERMINED AREA OF A SURFACE

[75] Inventor: Graham Morley Clarke, Edinburgh, Scotland

[73] Assignee: Ferranti, Limited, Hollinwood, England

[22] Filed: May 27, 1975

[21] Appl. No.: 580,567

[30] Foreign Application Priority Data

May 28, 1974 United Kingdom ............. 23570/74

[52] U.S. Cl. .................................. 356/200; 250/563
[51] Int. Cl.[2] .................. G01N 21/16; G01N 21/32
[58] Field of Search .......... 250/562, 563, 572, 560; 356/200, 237, 159, 160, 163, 199

[56] References Cited

UNITED STATES PATENTS

| 3,061,731 | 10/1962 | Thier et al. | 250/563 |
| 3,584,963 | 6/1971 | Wisner | 250/563 X |
| 3,646,353 | 2/1972 | Bhullar et al. | 356/200 X |
| 3,825,765 | 7/1974 | Schober et al. | 356/200 X |

FOREIGN PATENTS OR APPLICATIONS 1,473,503   7/1962   Germany ........................... 250/563

*Primary Examiner*—Alfred E. Smith
*Assistant Examiner*—T. N. Grigsby
*Attorney, Agent, or Firm*—Cameron, Kerkam, Sutton, Stowell & Stowell

[57] ABSTRACT

A circuit arrangement for use with a scanned-beam moving-surface blemish detector uses the detection of leading-and trailing-edges of the surface in each scan to provide in the following scan a margin or margins, the separation of which provides a measure of the surface width over which detection can take place without the edges being detected as faults. In a modification the margins are extended to the direction of surface movement by introducing a minimum width, between leading-and trailing-edge margins, which must exist before fault detection is permitted.

12 Claims, 6 Drawing Figures

DETECTION OF FAULTS IN A PREDETERMINED AREA OF A SURFACE

This invention relates to the detection of faults in a predetermined area of a surface and in particular to circuit arrangements associated with such detection.

The type of detector with which this invention is concerned is one in which a surface is movable relative to the detector and comprises a source of a beam of optical radiation, means operable to scan the beam repetitively across the surface between leading and trailing edges of the surface transversely to the direction of motion of the surface, and detection means operable to collect optical radiation reflected from, or transmitted by, the surface and to produce, in response to a change in the radiation collected, a detection signal indicative of the presence of a fault. Such a detector of faults will hereinafter be referred to as being "of the type stated". The terms "optical radiation" and "light" include electromagnetic radiation in the visible, infra-red and ultra-violet parts of the spectrum.

In detectors of the type stated it is possible for changes in radiation, caused by the beam engaging or leaving the edges of the surface, to produce a detection signal unless provision is made to restrict operation of the detection means to provide a detection signal only when the beam is in engagement with the surface. In each scan of the beam the position of a leading edge at which the beam engages the surface is characterised by the first detection signal produced, and, if a large contrast exists between the surface and the background, by the large amplitude of the detection signal; this leading edge signal may be used to permit operation of the detection means.

A similarly produced signal in respect of a trailing edge, at which the beam leaves the surface, is less satisfactory in that it will be of the same amplitude as a fault comprising a hole through the surface and it cannot be employed to inhibit operation of the detection means until after its detection.

Where the area of surface for which detection is to take place is of constant width, operation of the detection means can be inhibited a predetermined time after the leading-edge signal is produced, such that the trailing-edge is not detected and the detected signal interpreted as a fault. If the surface undergoes a change in width, or if the surface has a border of variable width, then the point at which operation of the detection means has to be inhibited cannot be determined from the leading-edge signal alone.

It is an object of the present invention to provide a circuit arrangement for use with a detector of the type stated operable to control fault detection over a predetermined area of a movable surface.

According to one aspect of the present invention a circuit arrangement for use with a detector of the type stated comprises edge detection means for producing edge signals in response to the detection of the leading- and trailing-edges of the surface, control means operable to produce a first signal in response to the detection of the leading-edge, and a second signal in response to the detection of the trailing-edge, said second signal defining in relation to the traverse speed of the beam a trailing-edge margin, the width of which is greater than any anticipated variation in the position of the trailing-edge of the surface between successive scans, and output means responsive to a detection signal occurring in the time interval between a first signal and the subsequent second signal to indicate the presence of a fault.

The circuit arrangement may include inhibit means operable to inhibit the output means until the time interval between the first signal and the second signal exceeds a predetermined minimum value in any one scan.

The control means may include delay means responsive to the detection of the trailing-edge in one scan to provide said second signal in the next following scan. The delay circuit may comprise a monostable circuit operable to be triggered to its unstable state by said detection of the trailing-edge in one scan and to produce said second signal by returning to its stable state in the next scan.

The circuit arrangement as defined in the three preceding paragraphs may also include verification means operable to inhibit said output means unless said first and second signals have been produced in sequence for a preset number of successive scans of the beam.

According to another aspect of the present invention a detector of faults in a surface movable relative to the detector, comprises a source of a beam of optical radiation, means operable to scan the beam repetitively across the surface between leading- and trailing-edges of the surface transversley to the direction of motion of the surface, and detection means operable to collect optical radiation reflected from, or transmitted by, the surface to produce, in response to a change in the radiation collected, a detection signal indicative of the presence of a fault, and a circuit arrangement including edge detection means for producing edge signals in response to the detection of the leading- and trailing-edges of the surface, control means operable to produce a first signal in response to the detection of the leading-edge, and a second signal in response to the detection of the trailing-edge, said second signal defining in relation to the traverse speed of the beam a trailing-edge margin the width of which is greater than any anticipated variation in the position of the trailing-edge of the surface between successive scans, and output means responsive to a detection signal occurring in the time interval between a first signal and the subsequent second signal to indicate the presence of a fault.

Figure 1B:
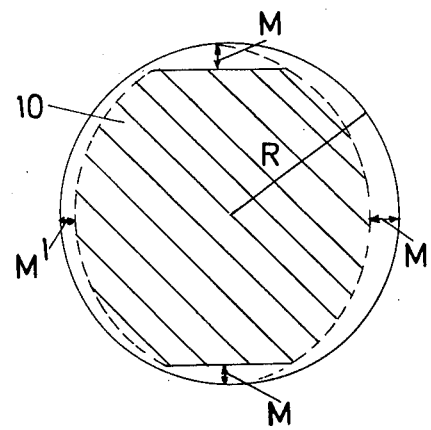
Figure 1C:
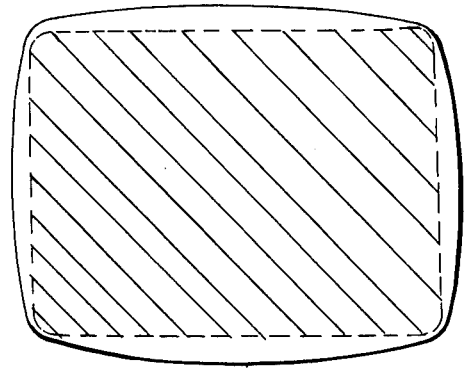
Figure 2:
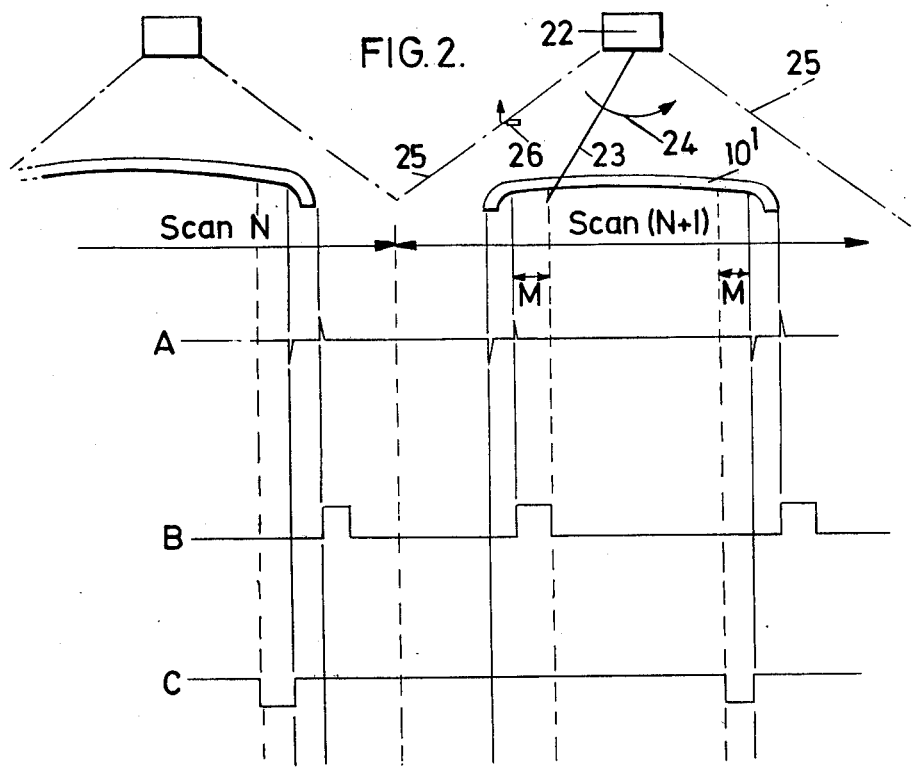
Figure 4:
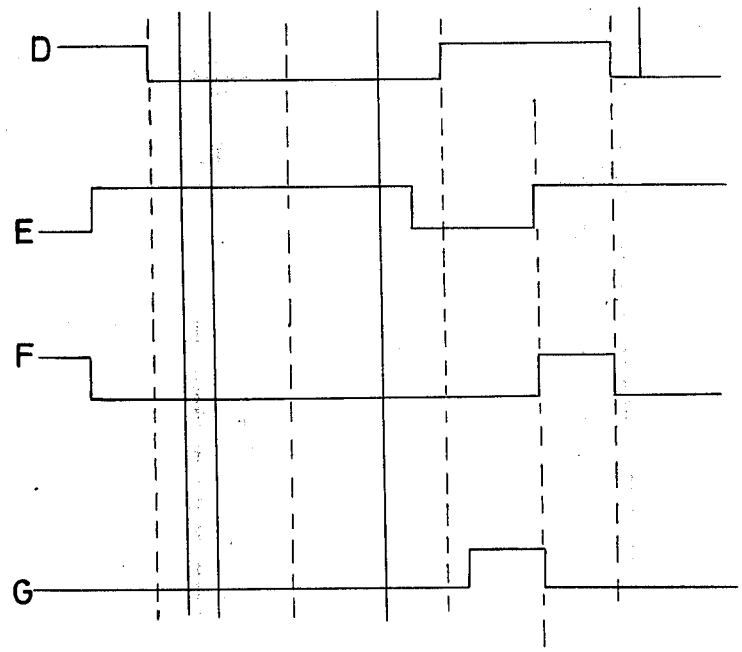
Figure 3:
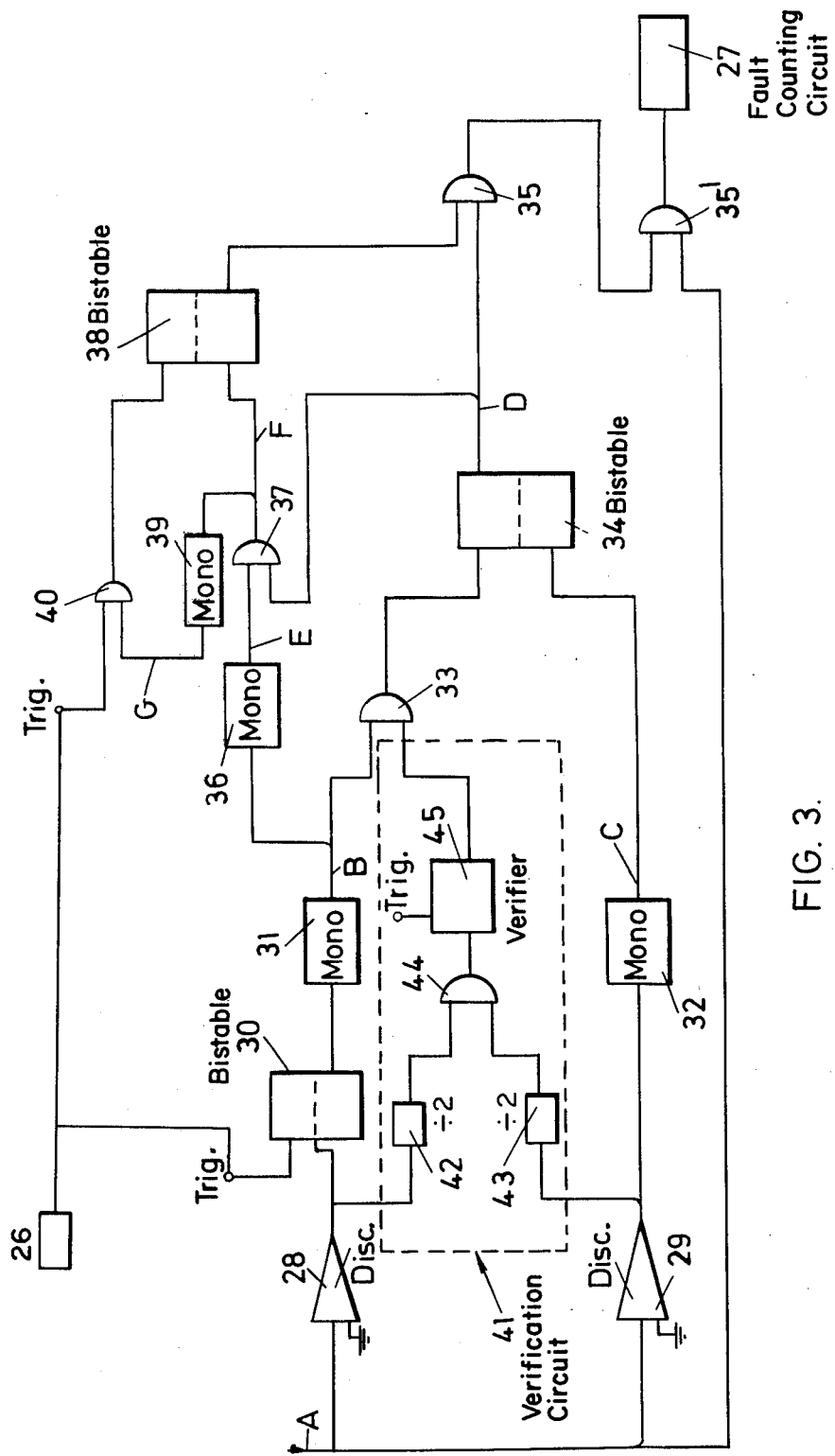

An embodiment of the present invention will now be described by way of example with reference to the accompanying drawings, in which:

FIGS. 1(a), 1(b) and 1(c) show plan views of objects to illustrate predetermined areas of the surfaces scanned for faults, FIG. 2 shows a sectional elevation of a scanning system of a detector of faults for use with the circuit arrangement of the present invention, FIG. 3 is a block diagram of a circuit arrangement according to the present invention, and FIG. 4 shows waveforms of signals appearing in the circuit arrangement of FIG. 3.

Referring to FIG. 1, FIG. 1(a) shows a plan view of an object 10 which is shown for convenience as being circular. The object is arranged to pass a scanning station (FIG. 2), containing the source of radiation, in the direction of the arrow 11 and to be scanned by a beam of radiation, say visible light, in a direction transversely to the direction of motion of the object. The paths of four successive scans are shown by lines 12 to 15 and extend between limits, shown at L, L, in a scan period of time $t$. Light reflected from, or transmitted by, the surface is collected and its level detected, any ʳ fault or discontinuity in the surface causing a change of the level of light collected and hence a detected signal.

Detection of faults should for efficient operation only be possible during the time that the beam is actually incident on the surface. As the beam crosses the leading-edge 16 and the trailing-edge 17, it produces signals which are detected as faults, so that fault detection must be limited to begin after the occurrence of the leading-edge signal and end before the occurrence of the trailing-edge signal.

The limitation is satisfied with respect to the leading-edge by discriminating the detected edge signal thereby producing a first signal (because of its large amplitude) and thereafter permitting operation of the detection means. The limitation is more difficult to satisfy with respect to the trailing-edge; if the detected trailing-edge signal is used directly to inhibit the detection means then unless it is a particularly sharp pulse, and can be merely subtracted from a count of detected signals due to faults in the scan, it is itself counted.

The elimination of the trailing-edge signal according to the present invention may be considered with respect to the circular object 10. The pulse is triggered at 18 in scan 12 and extends until the beam reaches point 19 in scan 13. A further pulse is triggered when the beam reaches the point 20 in scan 13 and extends until the beam reaches point 21 in scan 14. In each case the end of the pulse comprising a second signal is used to inhibit the detection means so that the trailing-edge signal is not counted. Because the width of the object, between leading- and trailing-edges, has contracted between adjacent scans; the trailing-edge at 20 is detected earlier in the scan than the edge at 18 so that the pulse ending at 21 and comprising the second signal occurs before the pulse at 19 by the same amount. Thus for the whole of the scanned object, there is a margin of width "M" in the direction of scan related to the traverse speed of the beam shown by broken line 17'.

It will be appreciated that adjacent scans may be separated and the relationship between the width M of the margin and the separation of successive scans must be chosen such that the width does not contract by an amount greater than, or equal to, M between successive scans. At a fixed scanning rate, the rate of change of width ($dw/dt$) must be less than ($M/t$). To satisfy this for large width changes the margin M must be made very large or the change in width per scan, that is, the line separation, must be as small as possible. For any individual object the width contracts to zero at the ends so to avoid an unacceptably large margin, adequate scanning is restricted by very close line separation if the trailing edge is not to be detected as a blemish. The scanning station is fixed in position so that the scanning line separation is directly proportional to the speed at which the object may be made to move past the scanning station and in order to reduce the line separation, this object passage time must be reduced to a low value.

If the passage time is unacceptably slow, the margin M may be extended to the front and back edges in the direction of scan as shown in FIG. 1(b). This effectively removes from the area of the surface to be scanned the parts where the width contraction is at its maximum, and scanning effectively takes place from when the surface exhibits a minimum value of width other than zero.

The principle may be applied to other, more complex, shapes such as a "rectangular" cathode-ray tube screen shown in FIG. 1(c). In such an object the width contracts rapidly at each end but varies only slightly over the rest of the area.

It will be readily appreciated that by extending the margin M to the front and back ends of the screen in the directions of motion the scanning line separation, and therefore the object speed, can be greatly increased over that possible without such margin.

In practice it is usually desirable to have a margin M' adjacent the leading-edge to prevent the detection means from being enabled until the large leading-edge signal has decayed to zero.

It may be desirable in certain circumstances to have the margin M' equal to the margin M at the other edges and for simplicity this arrangement will be considered. The area of the surface of a circular object for which fault detection can proceed is the shaded area shown in FIG. 1(b). The scanning rate and the speed of the object past the scanning station are determined from relationships between the dimensions of the object and the margin required so that to decide at what point the detection means is to operate, the time interval for which the beam is in contact with the surface for each scan is compared with, until it exceeds, that required to cross the surface at the minimum width, that is, until the time between the first signal and the second signal generated in the previous scan exceeds a predetermined duration. Thereafter, blemish counting can be started without the trailing-edge being detected as a fault.

A circuit arrangement for use with a detector employing the above principles of having a margin M extending around all edges of an object is shown in block form in FIG. 3 and described with reference to FIGS. 2 and 4.

The object 10' comprising a cathode ray tube screen is shown in section in FIG. 2 and passing a scanning station 22 in a direction perpendicular to the plane of the drawing. A beam of light 23, from the scanning station, is caused to scan the surface of the object in the direction of the arrow 24 between the limits of the scan denoted by the lines 25. A photo-detector 26 is placed in the path of the beam at the edge of the scan to provide a trigger signal at the beginning of each scan. During each scan, light is collected by detection means of the character described in the second paragraph of this specification (not shown), below the object, when the beam is either side of the object and when the beam is incident on the centre, transparent, portion, but no light is collected from the edges. For a blemish-free screen, the signal obtained by the detector is of the form shown in waveform A in FIG. 4 and in fact two such edge signals are produced for each leading- and trailing edge. The negative-going spikes are caused by a "light" — to — "dark" transition and the positive-going spikes are caused by a dark — to — light transition. The detected signal having the waveform A is fed to a counter of faults 27 and to the circuit arrangement, both shown in FIG. 3. The functions of the circuit will be explained with reference to the other waveforms of FIG. 4, which waveforms are of signals appearing at correspondingly lettered points in the circuit arrangement.

The signal A is fed to edge detection means comprising amplitude discriminators 28 and 29, one for each polarity of signal. The output of the discriminator 28 is fed by way of a bistable switch 30 to a monostable device 31 and the output of the discriminator 29 is fed directly to a monostable device 32. The bistable switch 30 is reset to give no output by the trigger signal from the photo-detector 26 at the start of each scan. The first positive going input pulse sets the switch and provides an output pulse to operate the monostable device 31. The monostable device produces a first signal B comprising a pulse whose duration defines the leading-edge margin. The negative going signal at the trailing-edge, as the beam leaves the surface, triggers the monostable device 32 to produce a second signal C, which second signal comprises a pulse extending until before the trailing-edge is detected on the next following scan, that is, to give a margin before the trailing-edge. The negative going signal produced at the trailing-edge defines the margin for the trailing-edge of the next scan. The negative going signal produced at the beginning of each scan is ineffective as the monostable device 32 is already triggered. The bistable switch 30 acts as a divide-by-2 circuit and the positive going pulse (at the end of the scan) merely resets it to zero. The trigger pulse is also injected to ensure the divide-by-2 starts in the right place when the signals are just becoming strong enough as the object passes the scanning station. Subsequent to this the trigger is unnecessary. The devices 30, 31 and 32 comprise the control means.

The first signal B is fed to output means by way of gate 33 to a SET input of a bistable switching circuit 34 and the second C, is fed directly to the RESET input, the switching circuit being triggered by the trailing edges of the signals. The output signal (D) of the switching circuit, produced when it is SET, is fed by way of a normally open gate 35 and gate 35' to energise a fault counting circuit 27; the signal D comprises a voltage pedestal.

As described above with respect to FIG. 1(b) the object is only scanned for blemishes between margins of M in the direction of motion of the object as well as the direction of scan, so that a minimum scan duration has to be measured before the fault counter is energised. That is, inhibit means is operable to inhibit the output means until the time interval between the first signal and the second signal exceeds a predetermined minimum value in one scan.

The signal B at the beginning of the leading-edge margin operates a monostable device 36 of the inhibit means and comprising delay means. The output of the device comprises minimum width signal E in the form of a pulse of zero level from a normally positive level having the minimum scan duration. The signal E is fed to an AND gate 37, comprising delay gating means, with the signal D so as to produce a signal F only after the time that the signal E has finished and until the pedestal signal D finishes, that is, for the part of the surface in excess of the minimum width. The signal F is fed to a second bistable switching circuit 38 to SET the switching circuit and produce an output which opens the gate 35 and thus the gate 35'. The signal F also operates a monostable device 39 which provides an output signal G (of zero level) for a duration slightly less than the duration of one scan. The signal G is fed to one input of trigger gating means comprising an AND gate 40, which gate also is arranged to receive as a second input a trigger signal from the trigger means, photodetector 26, at the start of each scan. The output of the gate 40 is connected to a reset input of the bistable switching circuit 39 to remove its output, close the gate 35 and inhibit the output means.

In operation, when the object first passes under the scanning beam, the pedestal D generated is not normally greater than the minimum duration of beam traverse time (determined by the duration of the signal E) and there is no signal F produced at the gate 37. Thus the signal G is not generated and when the trigger pulse is produced at the start of the next scan, the gate 40 is open and the bistable switching circuit 38 is reset, closing the gate 35. Only when the pedestal D exceeds the minimum duration is the bistable switching circuit 38 set and while remaining thus, the resetting mechanism is rendered inoperative.

The part of the circuit shown at 41 is employed to verify that edge signals have been properly produced and detected before the fault counter is allowed to be energised by the pedestal signal D.

The verification circuit comprises divide-by-2 circuits 42 and 43 connected to receive pulses from amplitude discriminators 28 and 29 respectively, and the outputs of these circuits are fed to an AND gate 44. When four pulses of the signal A (two of each polarity) have been received satisfactorily then the gate 44 produces a verified edge which is fed to a verifier 45. The verifier is also arranged to have as an input the trigger signal from the photodetector 26. In operation, the verifier compares the output of the gate 44 with the trigger signal at the start of each scan for a predetermined number of scans to determine that all edge pulses are being detected satisfactorily. Then the verifier produces an output signal to open the gate 33 and permit the pedestal signal D to be formed by signal B. Clearly, modifications to the detail of the verification circuit are possible when the input signals differ from those described but the principles will remain the same.

If conditions are not repeated for the predetermined number of scans then the inspection does not start. In practical apparatus verification period of the first ten scans may be chosen to cause a margin of 1%, comparable with the intended margin M.

For more complex shapes than the circular one illustrated in FIGS. 1(a) and 1(b) geometrical relationships may be obtained between the change in position of the edge and the position of the object in relation to the scanning beam to derive the optimum margins. Alternatively, it is possible to assess the above optima by passing the objects by the scanning apparatus at a given speed and reducing the margin progressively (or vice versa) until a faultless object will not produce a verified pedestal signal.

The invention is not restricted to the detection of faults in a predetermined area of a plane surface and can be used where a pattern or other embellishment surrounds the predetermined area. The width of the margin is chosen to include all of the pattern leaving the central area in which faults can be detected.

The above description has been directed towards the detection of light by transmission through an object, but the apparatus may, of course, employ reflection from an object.

What I claim is:

1. A detector of faults in a surface movable relative to the detector, the detector comprising a source of a beam of optical radiation, means operable to scan the beam repetitively across the surface between leading and trailing edges of the surface transversely to the direction of motion of the surface, and detection means operable to collect optical radiation reflected from, or transmitted by, the surface to produce, in response to a change in the radiation collected, a detection signal indicative of the presence of a fault, and a circuit arrangement including edge detection means for producing edge signals in response to the detection of the leading- and trailing-edges of the surface, control means operable to produce a first signal in response to the detection of the leading-edge, and a second signal in response to the detection of the trailing-edge, said second signal defining in relation to the traverse speed of the beam a trailing-edge margin the width of which is greater than any anticipated variation in the position of the trailing-edge of the surface between successive scans, and output means responsive to a detection signal occurring in the time interval between a first signal and the subsequent second signal to indicate the presence of a fault.

2. A circuit arrangement for use with a detector of faults in a surface movable relative to the detector, the detector comprising a source of a beam of optical radiation, means operable to scan the beam repetitively across the surface between leading and trailing edges of the surface transversely to the direction of motion of the surface, and detection means operable to collect optical radiation reflected from, or transmitted by, the surface to produce, in response to a change in the radiation collected, a detection signal indicative of the presence of a fault, the circuit arrangement including edge detection means for producing the edge signals in response to the detection of the leading- and trailing-edges of the surface, control means operable to produce a first signal in response to the detection of the leading-edge, and a second signal in response to the detection of the trailing-edge, said second signal defining in relation to the traverse speed of the beam a trailing-edge margin the width of which is greater than any anticipated variation in the position of the trailing-edge of the surface between successive scans, output means responsive to a detection signal occurring in the time interval between a first signal and the subsequent second signl to indicate the presence of a fault, and inhibit signal operable to inhibit the output means until the time interval between the first signal and the second signal exceeds a predetermined minimum value in any one scan.

3. A circuit arrangement as claimed in claim 2 in which the control means includes delay means responsive to the detection of the trailing-edge in one scan to provide said second signal in the next following scan.

4. A circuit arrangement as claimed in claim 3 in which the delay means comprises a monostable circuit operable to be triggered into an unstable state by said detection of the trailing-edge in one scan and to produce said second signal by returning to its stable state in the next scan.

5. A circuit arrangement as claimed in claim 2 in which the edge detection means comprises for each polarity of detection signal an amplitude discriminator providing a threshold level set to pass signals having an amplitude characteristic of the detection of edges but to reject signals due to the detection of faults.

6. A circuit arrangement as claimed in claim 2 in which the output means comprises a first bistable switching circuit operable to be SET to provide an output signal by said first signal and to be RESET to provide no output signal by said second signal and gating means responsive to an output of the bistable switching circuit to pass through the gating means said detection signals.

7. A circuit arrangement as claimed in claim 2 in which the inhibit means comprises a second bistable switching circuit operable to be SET to produce an inhibit signal to be applied to the output means and to be RESET to provide no signal, trigger means operable to provide a trigger signal at the start of each scan of the beam, trigger gating means operable when opened to pass the trigger signal to RESET the bistable means, delay means responsive to the first signal to produce a minimum width signal after a predetermined delay, and delay gating means responsive to the minimum width signal occurring in the time interval between a first signal and the subsequent second signal to SET the bistable switching circuit and to close the trigger gating means until after the trigger signal has been produced in the next following scan.

8. A circuit arrangement as claimed in claim 7 in which the delay means comprises a monostable circuit operable to be triggered into an unstable state by said first signal and to produce said minimum width signal by its return to its stable state.

9. A circuit arrangement as claimed in claim 2 in which the control means includes delay means responsive to its detection of the leading-edge to produce said first signal after a predetermined delay related to the traverse speed of the beam to define a leading-edge margin.

10. A circuit arrangement as claimed in claim 9 in which the delay means comprises a monostable circuit operable to be triggered into an unstable state by the detection of said leading-edge.

11. A circuit arrangement as claimed in claim 2 including verification means operable to inhibit said output means unless said first and second signals have been produced in sequence for a preset number of scans of the beam.

12. A circuit arrangement as claimed in claim 11 in which the verification means comprises means operable to receive said edge signals and to provide a verified edge signal when the anticipated number of edge signals have been produced in each scan and counter means operable to count the verified edge signals for said preset number of scans to give a verification output signal when the correct number have been counted and gating means operable to inhibit the output means until a verification output signal is produced.

* * * * *

UNITED STATES PATENT OFFICE
CERTIFICATE OF CORRECTION

Patent No. 4,014,615                Dated March 29, 1977

Inventor(s) Graham Morley Clarke

It is certified that error appears in the above-identified patent and that said Letters Patent are hereby corrected as shown below:

Column 7, line 41, "signal" should read --means--.

Signed and Sealed this

Eleventh Day of October 1977

[SEAL]

Attest:

RUTH C. MASON
*Attesting Officer*

LUTRELLE F. PARKER
*Acting Commissioner of Patents and Trademarks*